United States Patent [19]

Robinson

[11] Patent Number: 4,956,480

[45] Date of Patent: Sep. 11, 1990

[54] 7-AMINO-4-METHYL-COUMARIN-3-CARBOXYALKYL DERIVATES AND FLUORESCENT CONJUGATES THEREOF

[75] Inventor: Don Robinson, Brackenwood, Great Britain

[73] Assignee: BioCarb AB, Sweden

[21] Appl. No.: 203,453

[22] PCT Filed: Dec. 2, 1986

[86] PCT No.: PCT/SE86/00550
§ 371 Date: Jun. 17, 1988
§ 102(e) Date: Jun. 17, 1988

[87] PCT Pub. No.: WO87/03589
PCT Pub. Date: Jun. 18, 1987

[30] Foreign Application Priority Data

Dec. 3, 1985 [SE] Sweden .................. 8505716

[51] Int. Cl.$^5$ .............. C07D 311/02; C07H 15/00
[52] U.S. Cl. .................. 549/288; 530/360; 530/409; 536/18.2
[58] Field of Search .............. 549/288; 530/360, 409; 536/18.2

[56] References Cited

U.S. PATENT DOCUMENTS 3,008,969 11/1961 Pretka .................. 549/288

FOREIGN PATENT DOCUMENTS 0522581 3/1956 Canada .................. 549/288

OTHER PUBLICATIONS

CA 97:49239b Goya et al., New Fluoresence Probes for Drug–Albumin Interaction Studies, 1982, Chem. Pharm Bull.

Primary Examiner—Mary C. Lee
Assistant Examiner—Catherine S. Kilby Scalzo
Attorney, Agent, or Firm—Burns, Doane, Swecker & Mathis

[57] ABSTRACT

A novel compound having the formula (I):

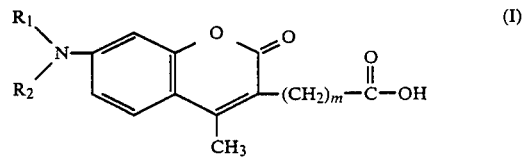

or a reactive derivative or functional equivalent thereof, wherein m is an integer from 1 to 4, and $R_1$ and $R_2$ are same or different and selected from hydrogen and 1-4C alkyl; a fluorescent conjugate having the formula (III):

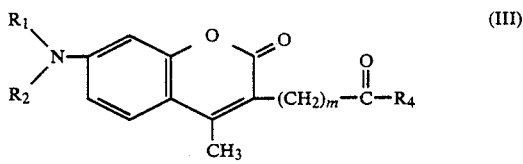

wherein m $R_1$ and $R_2$ have the meaning given in claim 1, and $R_4$ is a substituent attached to the keto group of formula (III) by a covalen bond. The new compounds and conjugates are useful as fluorescent labelling agents.

5 Claims, 7 Drawing Sheets

7-AMINO-4-METHYL-COUMARIN-3-CARBOXY-ALKYL DERIVATES AND FLUORESCENT CONJUGATES THEREOF

The present invention relates to new and novel compounds for use as fluorescent labelling agents and the invention also includes fluorescent conjugates of such new compounds.

Use of derivatives of 7-hydroxy coumarin for fluorometric assay of biologically active substances, such as enzymes is known. The labelling of such biologically active substances usually takes place by covalent coupling of the labelling agent to the substance involved. The use of 7-hydroxy coumarin derivatives in fluorometric assays is, however, subject to serious drawbacks, in view of the fact that the fluoroescence is developed only in the alkaline pH-range, usually above about pH 8. This is due to the fact that in order to develop fluorescence the hydroxyl group at the 7-position must be ionized. Since sensitive biological materials are involved in the assay the need to make the solutions alkaline before reading the fluorescence can constitute a factor that causes loss of sensitivity due to the necessary dilution with the alkaline reagents.

Another drawback of using known fluorescent labelling agents, such as fluorescein isothiocyanate (FITC) is that they emit radiation in a wavelength region that makes it difficult to distinguish from radiation emitted by autofluorescence of the biological material, such as cells or tissues. This autofluorescence of biological materials is often in the same yellow or green region, and the experimentator must make a subjective assessment as to whether he is examining true labelling characteristics or characteristics due to autofluorescence.

Yet another drawback of using 7-hydroxy coumarin derivatives is the fact that covalent coupling of for example 7-hydroxy coumarin-3-acetic acid to a polypeptide results in blocking of an amino group of the polypeptide with concomitant change of its acid-base balance. Such change may well cause alteration of the biological characteristics of the protein.

The invention has for its purpose to provide new coumarin derivatives, the use of which does not involve the implications of the known techniques as indicated above.

Another object of the invention is to provide fluorescent conjugates containing such new coumarin derivatives.

Still another object is to provide fluorescent labelling compounds emitting in a different region than the region of autofluorescence of biological material, such as cells and tissues.

In the instant disclosure the coumarin nucleus will be numbered as shown below, the numbering being given to facilitate the understanding of the following disclosure:

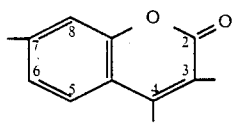

To attain these other and objects the invention provides for new and novel compounds having the formula (I).

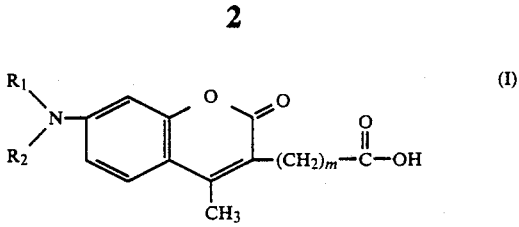

In this structural formula it is preferred that m is 1 or 2, and particularly 1 corresponding to the 3-acetic acid derivative. For practical reasons reactive derivatives involving the carboxyl function of compounds (I) are preferred, such as esters, for example N-hydroxysuccinimidyl esters, the reason being to facilitate covalent coupling to the biologically active material of interest.

Accordingly, the compounds of the invention preferably have the following formula (II):

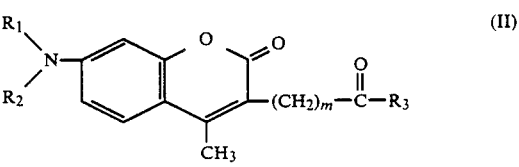

wherein $R_3$ is an N-oxysubstituent, such as an N-oxysuccinimide substituent. $R_3$ may also, of course, be hydroxy.

The invention also provides for new fluorescent conjugates having the formula (III):

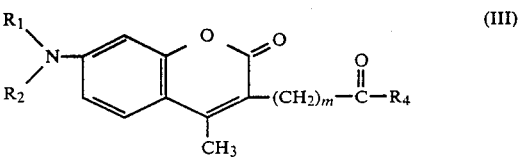

In this formula (III) $R_4$ may be an organic residue, such as a protein residue or carbohydrate residue.

In the above the formulas I-III, $R_1$ and $R_2$ may be the same or different and are selected from hydrogen and lower alkyl. By teh expression "lower" is meant groups containing 1 to 4 carbon atoms. Compounds I and II, wherein $R_1$ and $R_2$ both are different from hydrogen are preferred in that substitution on the nitrogen atom prevents polymerization between identical molecules to form amide bonds.

In regard to compounds of the formula (II) $R_3$ may be such as to result in reactive acyl derivatives, such as halides particularly acyl chloride.

In regard to fluorescent conjugates having formula (III) $R_4$ may be any organic residue of interest, such as a protein residue attached by an amide bond or a carbohydrate residue covalently attached to the keto group.

Compounds according to the invention are particularly useful as fluorescent labelling agents emitting in the blue region resulting in obvious advantages considering the drawbacks of the prior art as indicated above.

The invention will in the following be illustrated by specific but non-limiting examples with reference to the appended drawings wherein FIG. 1 illustrates the synthesis of 7-amino-4-methyl-coumarin-3-acetic acid wherein (A) is ethylchloroformate; (B) is m-aminophenol; (C) is 3-carbethoxyaminophenol; (D) is diethylacetyl succinate; (E) is 7-carbethoxyamido-4-methylcoumarin-3-ethyl acetate; (F) is 7-carbethoxyamido-4-methylcoumarin-3-acetic acid; (G) is 7-amino-4-methylcoumarin-3-acetic acid; (I) is alcoholic KOH (hydrolysis); and (II) is glacial acetic acid and concentrated sulphuric acid (hydrolysis);

EXAMPLE 1

The synthesis of 7-amino-4-methylcoumarin-3-acetic acid Preparation of carbethoxyaminophenol.

To 54.5 g (0.5 mol) of m-aminophenol (Aldrich Chemical Co., U.K.) dissolved in 375 ml of hot ethylacetate, 30 ml of ethylchloroformate (ethylchlorocarbonate 0.3 mol, BDH Chemicals, U.K.) were added over a 30 minutes period while refluxing. After an additional 10 minutes, the mixture was cooled, the suspension was filtered, and the filter cake was washed with ethyl acetate. The filtrate was allowed to stand for 24 hours at room temperature before the solvent was removed in vacuo. The solid was washed with petroleum ether and dried in vacuo.

Preparation of 7-carbethoxyamido-4-methylcoumarin-3-ethyl acetate.

The following mixture was then stirred for 3 hours at 25° C.: 108 ml of 75% sulphuric acid, 32.4 g (0.15 mol) of diethylacetyl succinate (Aldrich Chemical Co., U.K.) and 27.2 g (0.15 mol) of 3-carbethoxyaminophenol. After addition of 670 ml of ice-water, the suspension was filtered and the filter cake was thoroughly washed with cold water until the washings were neutral. The cake was washed finally with cold absolute alcohol and dried in vacuo.

Preparation of 7-carbethoxyamido-4-methylcoumarin-3-acetic acid.

20 g of ethyl ester above, was refluxed for 2 hours with 150 mls of 10% methanolic potassium hydroxide (w/v). The alcohol was removed by rotatory evaporation. A precipitate was formed by addition of 2M HCl, which was filtered off, washed with cold distilled water until the washing was free of acid, and dried in vacuo.

The hydrolysis of the above ester with methanolic potassium hydroxide was followed by thin layer chromatography (Merck aluminium sheets, Silica gel 60, Art 5553, BDH Chemicals, U.K.) using ethylacetate:methanol (90:10) as a developing solvent and was viewed under u.v. illumination at 350 nm. The unhydrolyzed ethylester above can be easily distinguished from coumarin acetic acid after hydrolysis, which moves with the solvent, while the latter remains at the origin.

Preparation of 7-amino-4-methylcoumarin-3-acetic acid.

Figure 1:
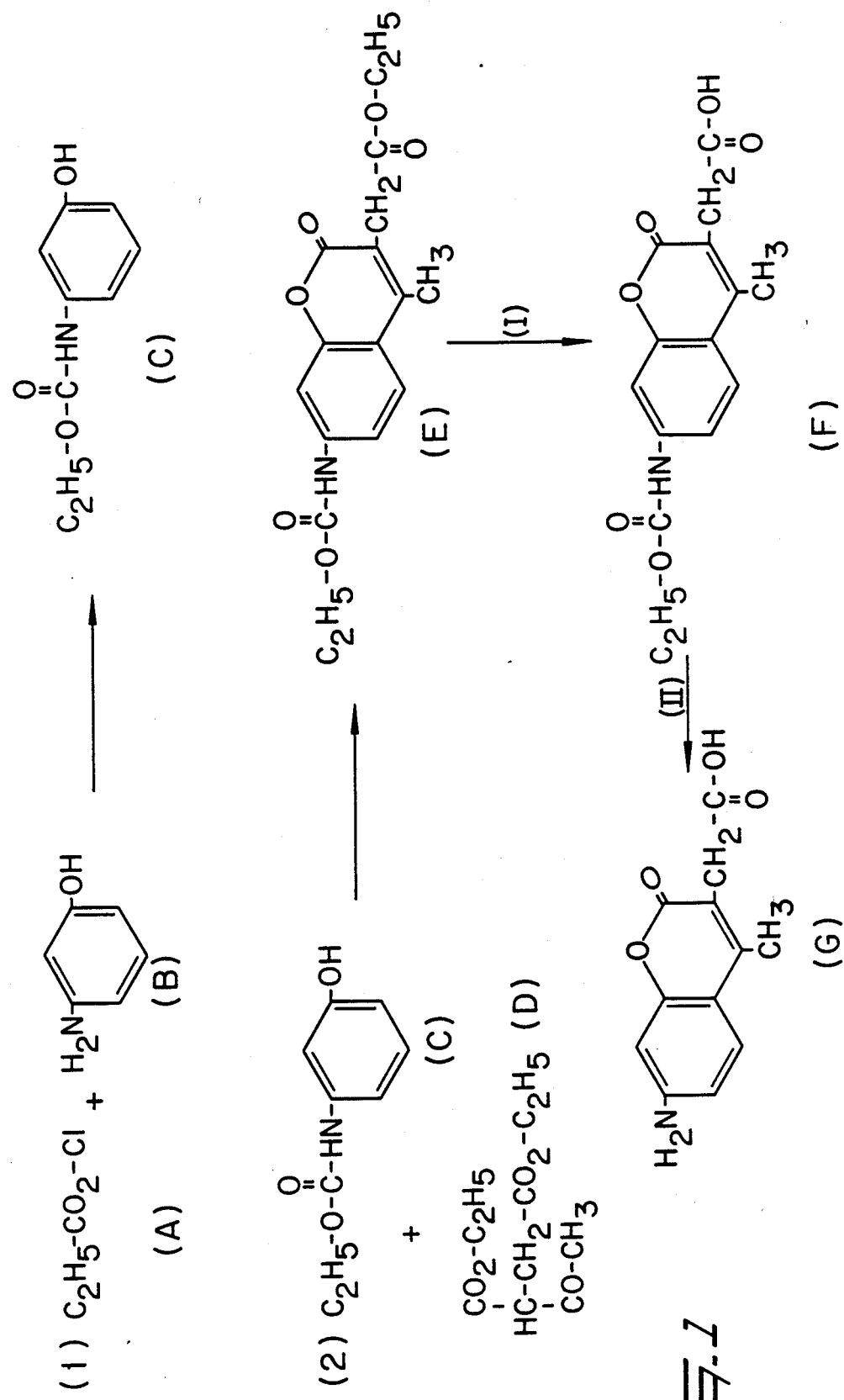

The carbethoxy group was removed as follows: 9.2 ml of glacial acetic acid, 8.2 ml concentrated sulphuric acid and 8.0 g of 7-carbethoxyamido-4-methylcoumarin-3-acetic acid were refluxed for 3 hours. After being cooled at 25° C., the mixture was poured into 120 ml of an ice-water mixture, then warmed to 70° C. and treated with Norit A-Celite (1:1) (BDH Chemicals, U.K.). After being filtered, warmed and washed with 180 ml of hot water, the filtrate was left to cool at room temperature to crystallize. The 7-amino-4-methylcoumarin-3-acetic acid crystals were filtered, washed with cold distilled water and then with cold ethanol. The crystals were left to dry in vacuo. The synthesis of 7-amino-4-methylcoumarin-3-acetic acid is summarized in FIG. 1.

Spectroscopic data and elemental analysis of 7-amino-4-methylcoumarin-3-acetic acid.

Nuclear magnetic resonance spectroscopy.

The 90 MHz $^1$H N.M.R. (DMSO-$d_6$) was in good agreement with the proposed structure of 7-amino-4-methylcoumarin-3-acetic acid, in which a singlet at $\delta$ 2.25 integrated for three protons was assigned to the methyl group at C-4, also another singlet was located at $\delta$ 3.48 for two protons and its chemical shift was typical for a methylene group at C-2. The primary amino protons appeared as a broad peak at $\delta$ 6.04, also the aromatic protons appeared at the typical chemical shift for the aryl ring protons, where H-5 appeared as a doublet at $\delta$ 7.46, H-6 as a double-doublet at $\delta$ 6.6 and H-8 as a singlet at $\delta$ 6.45.

Infra-red spectroscopy

Further characterization of the 7-amino-4-methylcoumarin-3-acetic acid was carried out by IR spectroscopy using an SP200 I.R. spectrometer. The IR spectrum showed the expected absorption of the primary $NH_2$ stretching bond at $\nu$ 3450 and $\nu$ 3360 wave numbers (cm$^{-1}$), and the C=O absorption appeared at $\nu$ 1685 wave number (cm$^{-1}$).

Elemental analysis

The melting point of 7-amino-4-methylcoumarin-3-acetic acid was above 305° C. Elemental analysis: Found C 60.07%; H 4.675%; N 5.675%; O 29.58%; $C_{12}H_{11}O_4N$, Required: C 61.80%; H 4.721%; N 6.00%; O 27.479%.

EXAMPLE 2

Preparation of 7-amino-4-methylcoumarin-3-acetic chloride

The reaction was carried out in a 500 ml two-necked reaction flask, containing 50 ml toluene, 7-amino-4-methylcoumarin-3-acetic acid (prepared as per Example 1 above), 699 mg (3 mmol) and thionyl chloride, 0.278 ml (446 ng, 3.75 mmol, BDH Chemicals, U.K.). Nitrogen was passed through the mixture during the reaction. The mixture was refluxed for 2 hours on an oil bath (temperature 130°-150° C.). The solvent was removed by rotatory evaporation and the precipitate was dried in vacuo.

Labelling of proteins using acyl chloride

A solution of the protein (1 g in 20 ml) is adjusted to pH 10 with NaOH and cooled in an ice bath. The 7-amino-methylcoumarin-3-acetyl chloride (125 mg) is added three portions with stirring over a 20 minutes period. The reaction mixture was kept at 4° C. for a further 3 hours, then centrifuged and dialysed overnight against 10 mM phosphate buffered saline pH 7.4 to remove excess reactants. A final purification by gel filtration can be carried out if necessay followed by freeze drying. The ester linked fluorescence (presumed to be tyrosine or serine residues) is relatively unstable at alkaline pH's and slowly hydrolyses on storage in solution.

EXAMPLE 3

Figure 2:
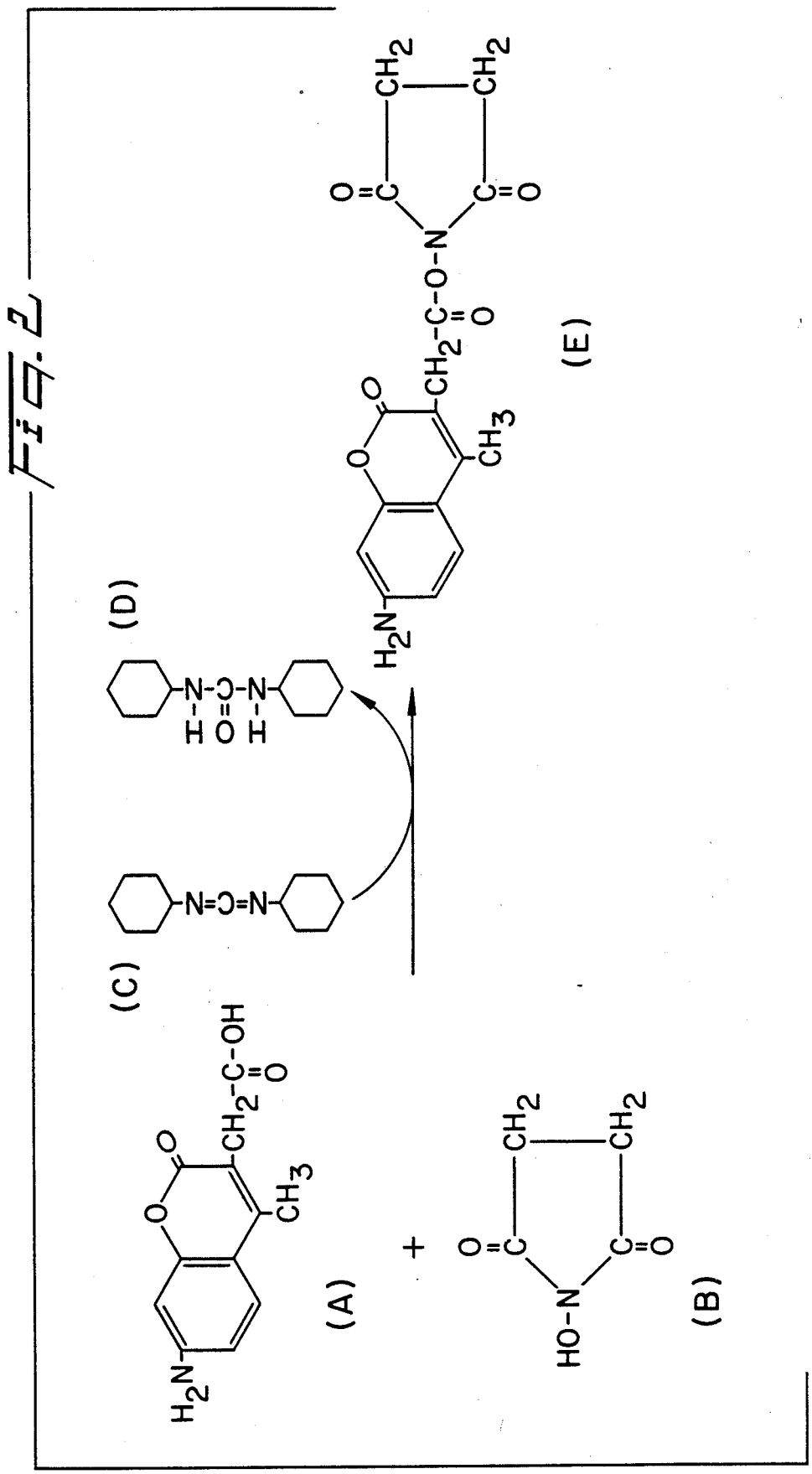
FIG. 2 illustrates the preparation of N-hydroxysuccinimide ester of 7-amino-4-methylcoumarin-3-acetic acid wherein (A) is 7-amino-4-methylcoumarin-3-acetic acid; (B) is N-hydroxysuccinimide; (C) is N-N'-dicyclohexylcarbodiimide; and (D) is dicyclohexylurea; and (E) is N-hydroxysuccinimide ester of 7-AMC-3-acetic acid.

Preparation of N-hydroxysuccinimide ester of 7-amino-4-methyl-coumarin-3-acetic acid 7-amino-4-methylcoumarin-3-acetic acid, 466 mg (2mmol) was dissolved in 10 ml of dimethylformamide (DMF). To the mixture was added 90 ml of tetrahydrofuran (THF) and 276 mg (2.4 mmol) of N-hydroxysuccinimide with cooling. To this 494 mg (2.4 mmol) of N,N'-dicyclohexylcarbodi-imide was added. The mixture was stirred overnight in the cold, and the dicyclohexylurea formed was then filtered off and the tetrahydrofuran was removed by rotatory evaporation. The N-hydroxysuccinimide ester was left to crystallize in dimethylformamide overnight in the cold. The crystals were washed with diethylether and the active ester so obtained was used without further purification. The preparation of the ester is summarized in FIG. 2.

EXAMPLE 4

General method of protein labelling

Casein labelled using the N-hydroxysuccinimide ester of 7-amino-4-methylcoumarin-3-acetic acid 1 g of casein was left to dissolve overnight in 20 ml of 50 mM sodium tetraborate buffer, pH 9.0. After removal of any undissolved particles by centrifugation, 99 mg of the above N-hydroxysuccinimide ester was added in three portions over a 1 hour period with vigorous stirring. The reaction mixture was kept at room temperature for a further 5 hours. The solution was then centrifuged, and the soluble fluorescent casein was precipitated by the addition of 0.5M sodium formate/HCl buffer, pH 4.0. The precipitate was filtered off and washed, first with the above buffer, and then with 10 mM phosphate-buffered saline (0.15M NaCl/10 mM sodium phosphate buffer), pH 4.0, until the washings were substantially free of fluorescence. Final traces of fluorescent contamination were removed by re-dissolving the labelled casein in 20 ml of 10 mM-phosphate buffered saline, pH 9.0, and dialysed overnight against a large volume of 10 mM phosphate buffered saline, pH 7.2, before freeze-drying the product.

The reaction of labelling casein (protein) was followed by thin layer chromatography (Merck Aluminium sheets, silica gel 60, Art 5553, BDH Chemicals, U.K.) using methanol:acetic acid (95:5) as a developing solvent and was viewed under u.v. illumination at 350 nm. The labelled protein can be easily distinguished from the uncoupled fluorophore, since it remains at the origin, while the free fluorophore moves with the solvent.

Further purification was achieved by redissolving the 7-amino-4-methylcoumarin-casein (1 g) in the minimum of phosphatebuffered saline (10 mM), pH 7.4, and applied to Sephadex G-25 (Pharmacia Fine Chemicals, Jppsala, Sweden), 2×45 cm column. The column was eluted with the same buffer, the active fractions not retained by the column were pooled, concentrated and dialysed before freeze-drying the product.

Figure 3:
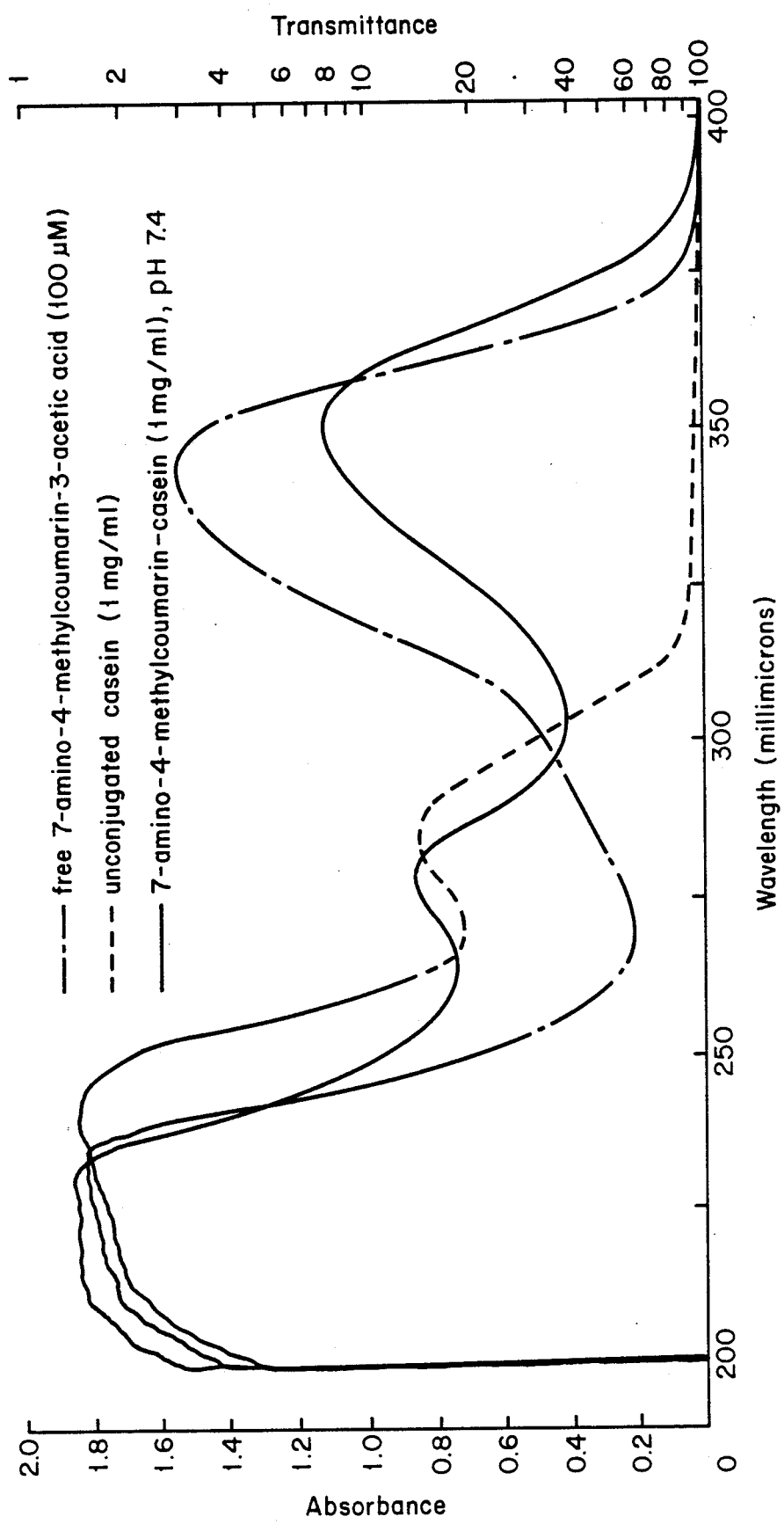
FIG. 3 illustrates absorbance spectra of a compound of this invention, of conjugated casein and of conjugate.

As before, the effectiveness of the fluorescent labelling procedure can be monitored by the appearance of a strong absorption band at 350 nm at pH 7.4 with solutions of the conjugated casein (see FIG. 3). Unconjugated casein has negligible absorbance under these conditions.

Again, assuming that the spectral characteristics of the fluorophore are not affected by conjugation, the conditions described above produce a degree of substitution of 0.070 $\mu$mol of 7-amino-4-methylcoumarin-3-acetic acid/mg of protein equivalent to approximately 1.6 basic amino acid residues being labelled on each molecule of casein.

EXAMPLE 5

Specific method for labelling lectins

Conjugation of Bandeiraea simplicifolia lectin with 7-amino-4-methylcoumarin-3-acetic acid 50 mg of Bandeiraea simplicifolia lectin was left to dissolve in 10 ml of 50 mM sodium tetraborate buffer, pH 9.0, containing 0.1 mM calcium chloride. 0.5 g of methyl-alpha-D-galactopyranoside (excess) was added to the above solution to protect binding sites and was left to stir for 30 minutes. To this, 20 mg of N-hydroxysuccinimide ester of 7-amino-4-methylcoumarin-3-acetic acid was added in three portions over a 1 hour period with vigorous stirring. The reaction mixture was left at room temperature for a further 5 hours. The solution was then centrifuged, and the soluble fluorescent lectin was dialysed against a large volume of 10 mM phosphate buffered saline, pH 7.0 (10 liters), containing 0.1 mM calcium chloride, before freeze-drying the product.

EXAMPLE 6

Hydrolysis of 7-amino-4-methylcoumarin-casein by proteases

Figure 4:
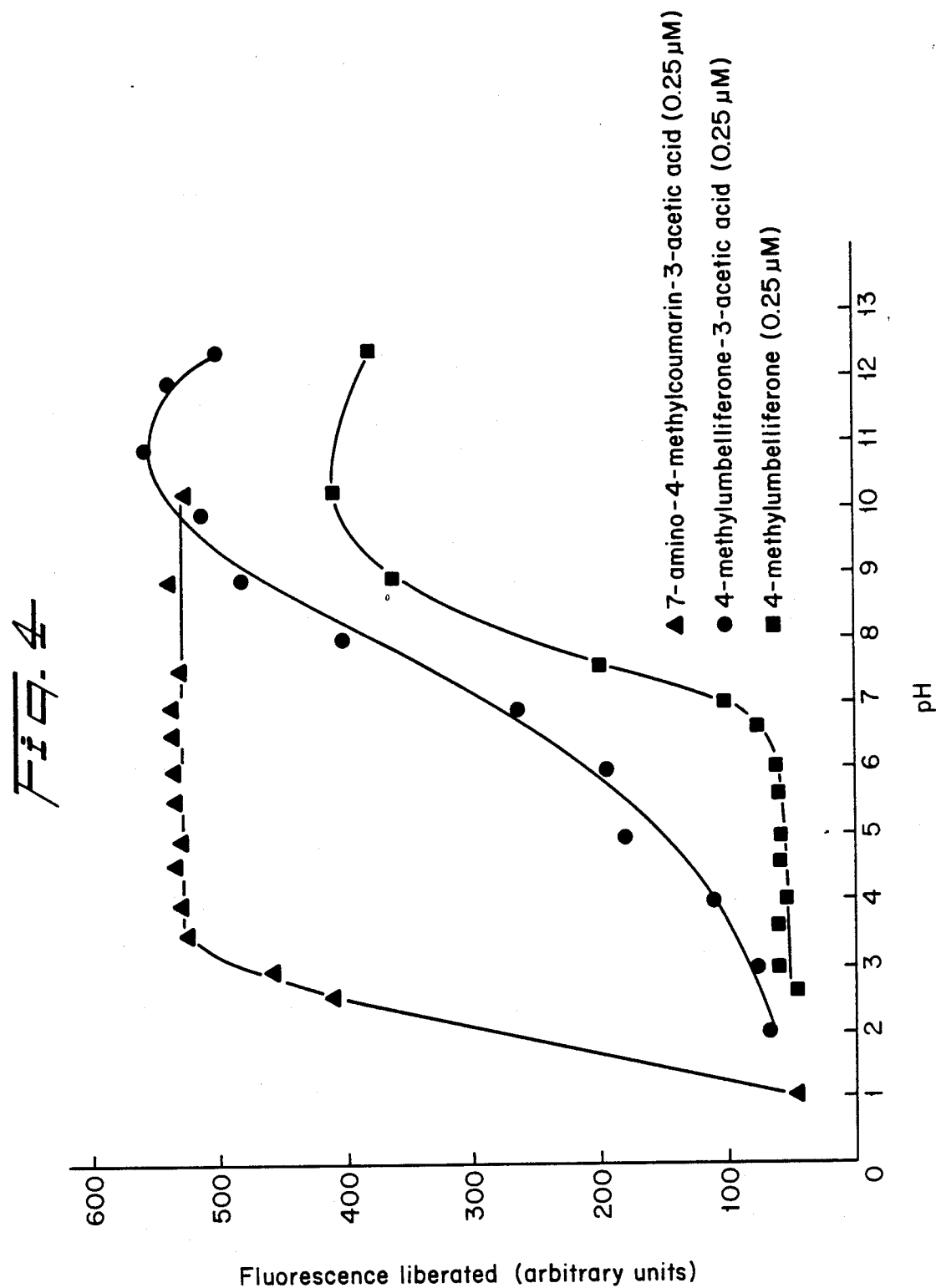
FIG. 4 is a diagram showing fluorescence as a function of pH.
Figure 5:
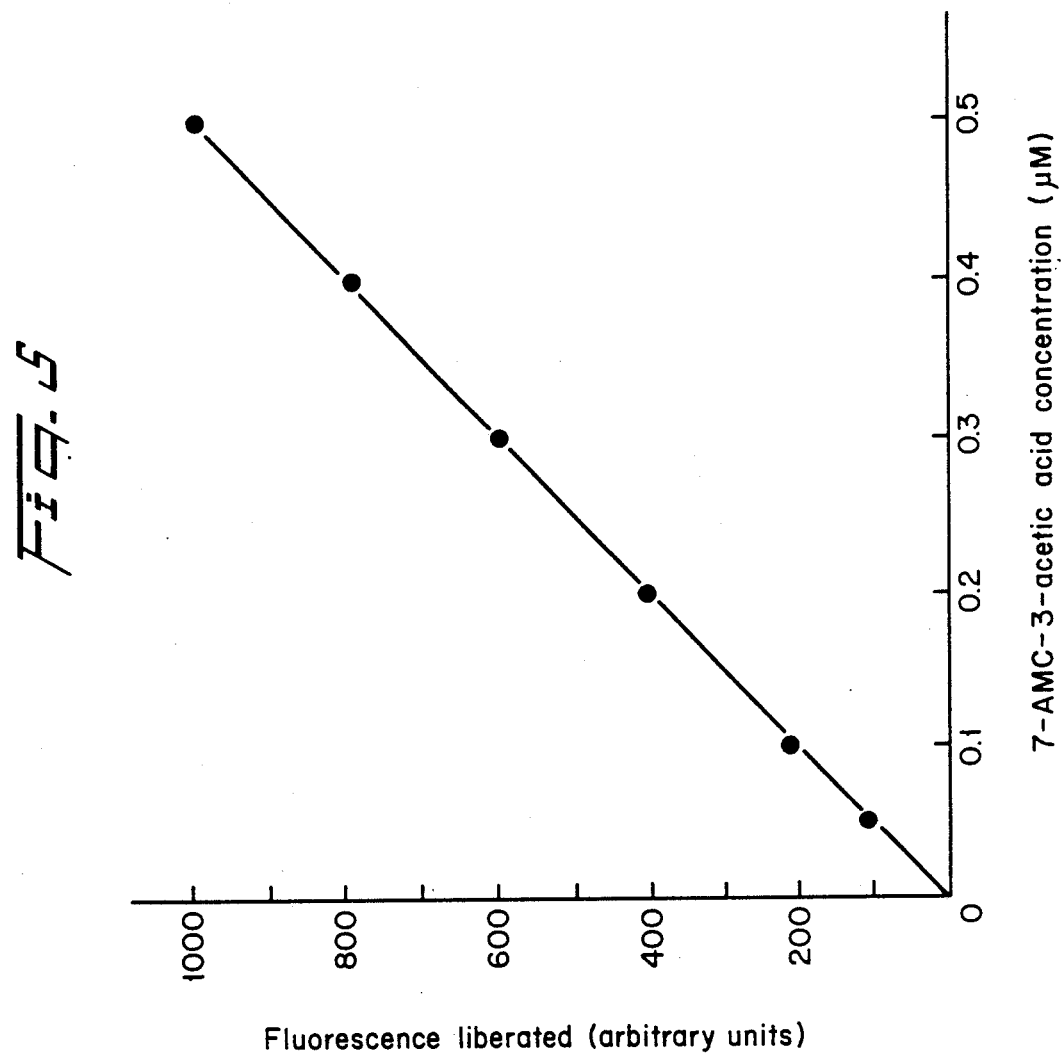
FIG. 5 shows a standard curve for fluorescence versus concentration.

The 7-amino-4-methylcoumarin-3-acetic acid fluorophore generates a maximum fluorescence over a wide range of pH, from 3.6 to 10.3 (see FIG. 4), and showed a linearity with different concentrations of 7-amino-4-methylcoumarin-3-acetic acid when the fluorimeter was set to read 1000 arbitrary units with a freshly-prepared 0.5 $\mu$m solution of the above fluorophor (cf. FIG. 5). The method of assay involves incubation at the optimum pH for proteinase activity, precipitation of unhydrolysed casein with trichloroacetic acid, followed by adjustment of a sample with sodium formate to pH 3.8 for fluorimetry, using the Locarte LMF fluorimeter.

To 80 $\mu$l of the appropriate assay buffer, was added 10 $\mu$l of enzyme solution. After equilibration at 37° C., 10 $\mu$l of a stock substrate solution was added (20 mg of 7-amino-4-methylcoumarincasein/ml in 10 mM phosphate-buffered saline, pH 7.4) to give a final substrate concentration of 0.2 mg in the assay mixture. After incubation for up to 30 minutes, the reaction was stopped and unhydrolysed substrate was precipitated by the addition of 0.5 ml of 5% (w/v) trichloroacetic acid. 2 ml of 0.5M sodium formate, pH 4.0, was added after 5 minutes of precipitation with trichloroacetic acid and was left for another 5 minutes at room temperature before filtration for fluorimetry.

Controls were performed by adding enzyme subsequent to incubation and trichloroacetic acid precipitation, and a suitable fluorescent standard, 0.5 μM solution of 7-amino-4-methylcoumarin-3-acetic acid in the above sodium formate buffer, set to read 1000 arbitrary units.

Figure 6:
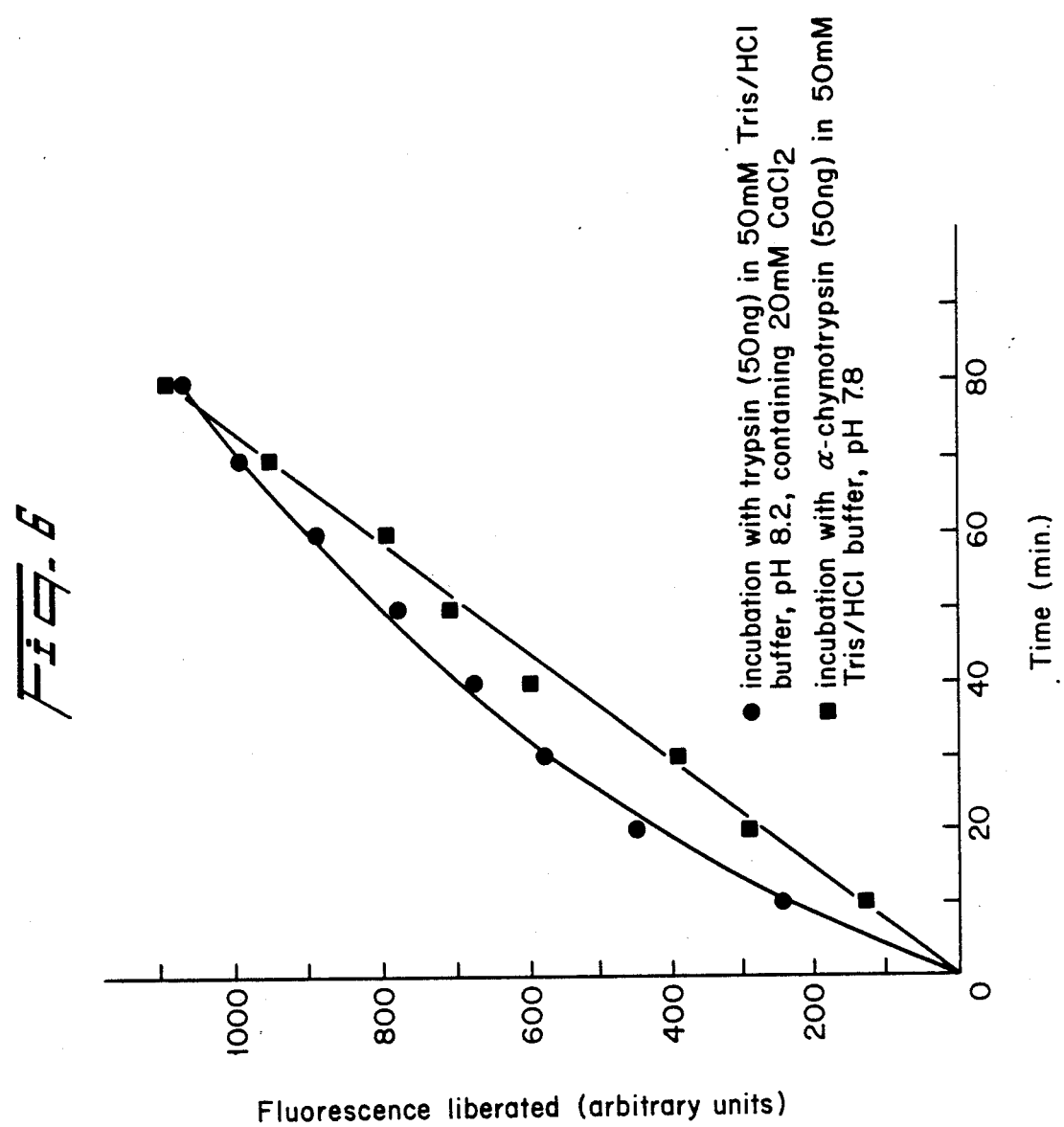
FIG. 6 shows fluorescence as a function of time in enzymatic hydrolysis of a conjugate.
Figure 7:
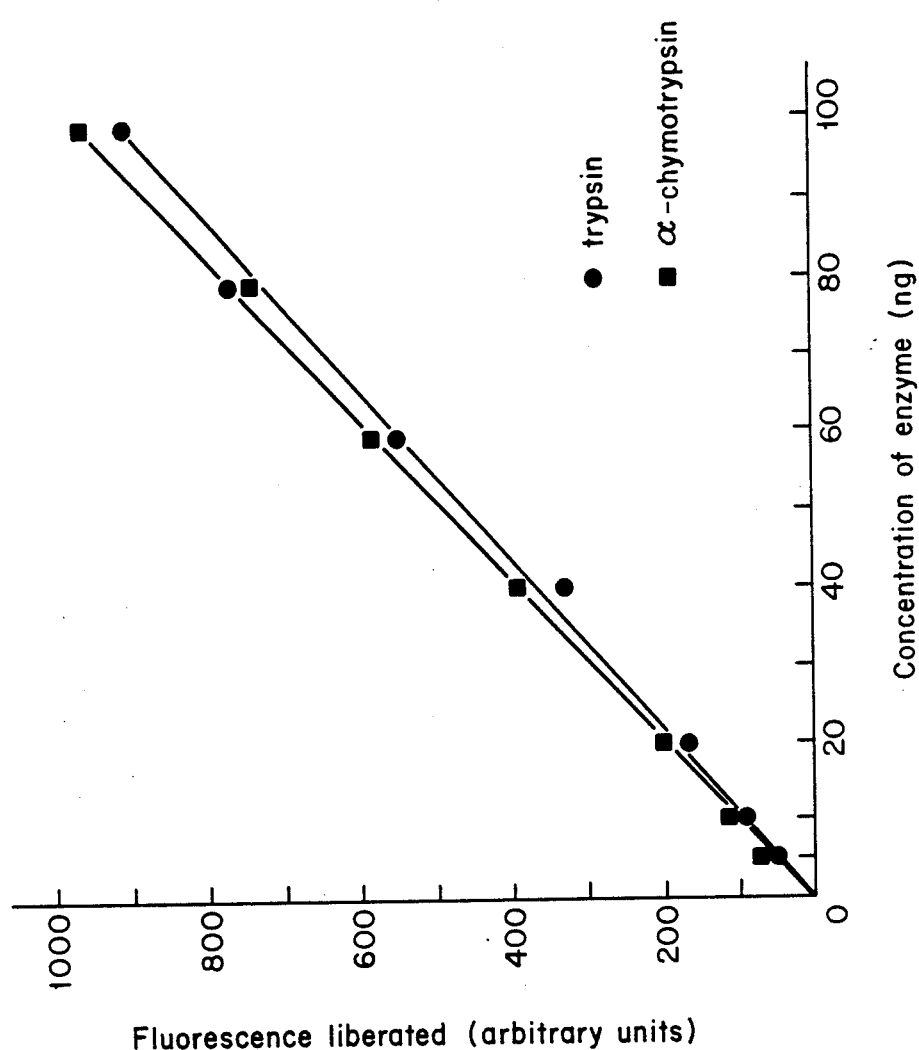
FIG. 7 shows a standard curve for digestion of a conjugate; fluorescence as a function of enzyme concentration.

When a low concentration os enzyme was used, the liberation of soluble fluorescent products was linear with time over a considerable period for alpha-chymotrypsin, whereas trypsin at low concentration and on longer incubation, may well result in some denaturation of the enzyme (cf. FIG. 6). Its stability increases in the presence of $CaCl_2$ and this agrees with the similar results obtained for the trypsin-like enzyme, plasmin, which undergoes autolytic alteration in solution. These initial rates of liberation are proportional to enzyme concentration (See FIG. 7). The sensitivity of the method under the above conditions of assay is such that 5 ng of trypsin or alpha-chymotrypsin is sufficient to produce a soluble fluorescence which can be measured after a 30 minutes incubation. Cathepsin B at concentrations as high as 2 μg of pure enzyme/assay mixture had no significant effect after incubations of up to 2 hours.

The present technique of using 7-amino-4-methylcoumarin-3-acetic acid as a fluorophor to label casein, compared to the 4-methylumbelliferone-3-acetic acid method, is approximately 10 times more sensitive, and the possibility, of the physical adsorbance of the proteases on their macromolecular substrates, which cause a lowering of activity, may be eliminated because the amount of substrate used in each assay for 7-amino-4-methylcoumarin-casein method is 10 times lower, 0.2 mg/assay, compared to the 4-methylumbelliferyl-casein method, 2 mg/assay.

EXAMPLE 7

Fabry's disease

Identification of carrier status by fluorescent lectin binding

Fabry's disease is a hereditary disorder of glycosphingolipid metabolism characterized by a deficiency of the lysosomal enzyme α-galactosidase A and the concomitant accumulation of galactose-terminal glycolipids in most tissues. The major storage product is ceramide trihexoside (Galα1-4 Galβ1-4 Glc β1-1'-cer).

This is an X-chromosome-linked disorder and because of the random nature of X-inactivation the persisting enzyme levels in various organs and tissues of female carriers may be very variable and are not diagnostically reliable. We therefore tested skin fibreblasts from patients and carriers of Fabry's disease along with cells from normal subjects for the specific accumulation of α-galactose-terminal storage products as a diagnostic indicator. Fibroblasts from patients, carriers and controls grown on coverslips were fixed with 3.5% paraformaldehyde in 10 mM-PBS, washed in PBS and treated with acetone/ethanol (1:1, v/v) at −20° C. for 40 minutes.

The fixed cells were then reacted for 20 minutes at room temperature with a solution of the labelled lectin (see Example 5) in phosphate buffer (175 mg/ml) at pH 7.0 in the presence of 0.1 mM-$CaCl_2$.

Controls to verify the specificity of the sugar binding were carried out in the same way but incorporating 10 mM-methyl-α-galactoside as a competitor during the binding process. Preparations were viewed by fluorescence microscopy, excitation 340–380 nm with suppresion at 430 nm.

Cells from Fabry patients demonstrated strong fluorescence that was completely abolished in the presence of methyl-α-glactoside, indicating that the lectin was selectively bound to the storage material. Little or no fluroescence could be observed in control fibroblasts from normal subjects.

Significant numbers of cells in the cultures from female carriers were also seen to have accumulated storage product on this evidence. Thus the method offers the possibility of identifying the carrier status of female siblings of Fabry hemizygotes on the basis of identification of a proportion of cells that react positively to the lectin. Lectin labelled with fluorescein isothiocyanata, proved to be an unsuitable reagent for staining the cells because of the native autofluorescence of the granules, which was hardly distinguished between the normal and the mutant cells in Fabry's disease,

EXAMPLE 8

Labelling anti-mouse antibodies 7-amino-4-methylcoumarin-3-acetic acid was used successfully to label anti-mouse antibodies to detect monoclonal antibody directed against the glomerular basement membrane of normal human kidney under the ultra-violet microscope.

I claim:

1. A compound having the formula (I):

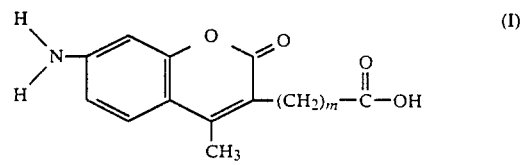

or an ester or halide thereof, wherein m is an integer from 1 to 4 hydrogen.

2. A compound according to claim 1, wherein m is 1 or 2.
3. A compound according to claim 1, wherein m is 1.
4. A compound having the formula (II):

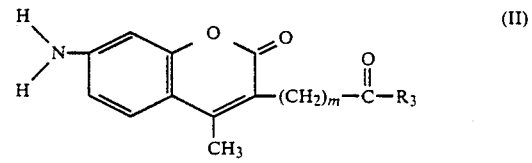

wherein m is an integer from 1 to 4 and $R_3$ is an N-oxysuccinimide substituent, a hydroxy substituent or a halogen substituent.

5. A compound according to claim 4, wherein $R_3$ is chloro.

* * * * *

REEXAMINATION CERTIFICATE (2136th)

United States Patent [19]
Robinson

[11] B1 4,956,480
[45] Certificate Issued Nov. 16, 1993

[54] 7-AMINO-4-METHYL-COUMARIN-CARBOXYALKYL DERIVATIVES AND FLUORESCENT CONJUGATES THEREOF

[75] Inventor: Don Robinson, Brackenwood, United Kingdom

[73] Assignee: BioCarb AB., Lund, Sweden

Reexamination Request:
No. 90/002,271, Feb. 6, 1991

Reexamination Certificate for:
Patent No.: 4,956,480
Issued: Sep. 11, 1990
Appl. No.: 203,453
Filed: Jun. 17, 1988

[22] PCT Filed: Dec. 2, 1986
[86] PCT No.: PCT/SE86/00550
§ 371 Date: Jun. 17, 1988
§ 102(e) Date: Jun. 17, 1988
[87] PCT Pub. No.: WO87/03589
PCT Pub. Date: Jun. 18, 1987

[30] Foreign Application Priority Data
Dec. 3, 1985 [SE] Sweden .................. 8505716

[51] Int. Cl.$^5$ .............. C07D 311/02; C07H 15/00
[52] U.S. Cl. ............... 549/288; 530/360; 530/409; 536/18.2
[58] Field of Search ............... 549/288; 530/360, 409; 536/18.2

[56] References Cited
U.S. PATENT DOCUMENTS
3,008,969 11/1969 Pretka .................. 549/288

OTHER PUBLICATIONS

Zimmerman, et al., Analytical Biochemistry vol. 70 pp. 258–262 (1976).
F. L. Williams–Chemical Abstracts vol. 57, 12440g–12441f (1962).
Rand–Weaver, et al., FEBS Letters vol. 182 (1) pp. 185–188 (Mar. 1985).
Angelides, et al., Journal Biol. Chem vol. 258 (19) pp. 11948–11957 (1983).

*Primary Examiner*—Marianne M. Cintins

[57] ABSTRACT

A novel compound having the formula (I):

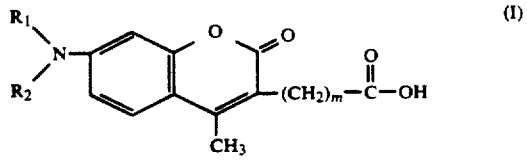

or a reactive derivative or functional equivalent thereof, wherein m is an integer from 1 to 4, and $R_1$ and $R_2$ are same or different and selected from hydrogen and 1–4C alkyl; a fluorescent conjugate having the formula (III):

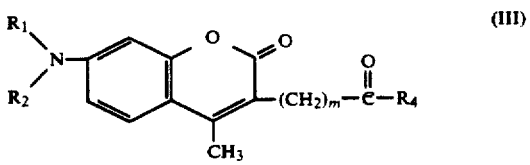

wherein m $R_1$ and $R_2$ have the meaning given in claim 1, and $R_4$ is a substituent attached to the keto group of formula (III) by a covalen bond. The new compounds and conjugates are useful as fluorescent labelling agents.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4–5 is confirmed.

Claim 1 is cancelled.

Claims 2 and 3 are determined to be patentable as amended.

New claim 6 is added and determined to be patentable.

2. A compound according to claim [1] *6*, wherein m is 1 or 2.

3. A compound according to claim [1] *6*, wherein m is 1.

*6. A compound having the formula (I):*

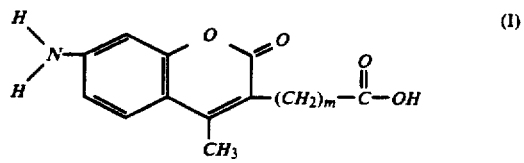

*or a halide thereof, wherein m is an integer from 1 to 4.*